(12) United States Patent
Brillon

(10) Patent No.: US 11,428,684 B2
(45) Date of Patent: *Aug. 30, 2022

(54) METHOD OF IDENTIFYING A SOURCE COMPONENT OF PARTICULATE DEBRIS IN AN AIRCRAFT ENGINE

(71) Applicant: PRATT & WHITNEY CANADA CORP., Longueuil (CA)

(72) Inventor: Louis Brillon, Varennes (CA)

(73) Assignee: PRATT & WHITNEY CANADA CORP., Longueuil (CA)

( * ) Notice: Subject to any disclaimer, the term of this patent is extended or adjusted under 35 U.S.C. 154(b) by 98 days.

This patent is subject to a terminal disclaimer.

(21) Appl. No.: 16/853,972

(22) Filed: Apr. 21, 2020

(65) Prior Publication Data

US 2021/0325362 A1    Oct. 21, 2021

(51) Int. Cl.
*G01M 15/14* (2006.01)
*G01N 33/28* (2006.01)

(52) U.S. Cl.
CPC ........ *G01N 33/2888* (2013.01); *G01M 15/14* (2013.01)

(58) Field of Classification Search
CPC .......................... G01M 15/14; G01N 33/2888
See application file for complete search history.

(56) References Cited

U.S. PATENT DOCUMENTS

| | | | |
|---|---|---|---|
| 5,986,546 A * | 11/1999 | Kramer | B60R 16/0232 188/1.11 R |
| 8,869,598 B2 | 10/2014 | Furman et al. | |
| 9,897,582 B2 | 2/2018 | Jean et al. | |
| 10,267,718 B2 | 4/2019 | Johnson | |
| 10,409,275 B2 | 9/2019 | Hagen et al. | |
| 2017/0248571 A1* | 8/2017 | Perreault | F01D 25/183 |
| 2020/0393082 A1* | 12/2020 | Jean | F16N 29/04 |
| 2021/0139040 A1* | 5/2021 | Ganiger | B60W 50/0205 |
| 2021/0325359 A1* | 10/2021 | Brillon | G01M 15/14 |

* cited by examiner

*Primary Examiner* — Eric S. McCall
(74) *Attorney, Agent, or Firm* — Norton Rose Fulbright Canada LLP

(57) ABSTRACT

The gas turbine engine can have a set of components, the components of the set all being made of material compositions of the same type having a common at least one main material element, the material compositions having distinct signatures in the form of a varying trace amount of one or more signature element, the distinct signatures varying from one component of the set to another.

15 Claims, 6 Drawing Sheets

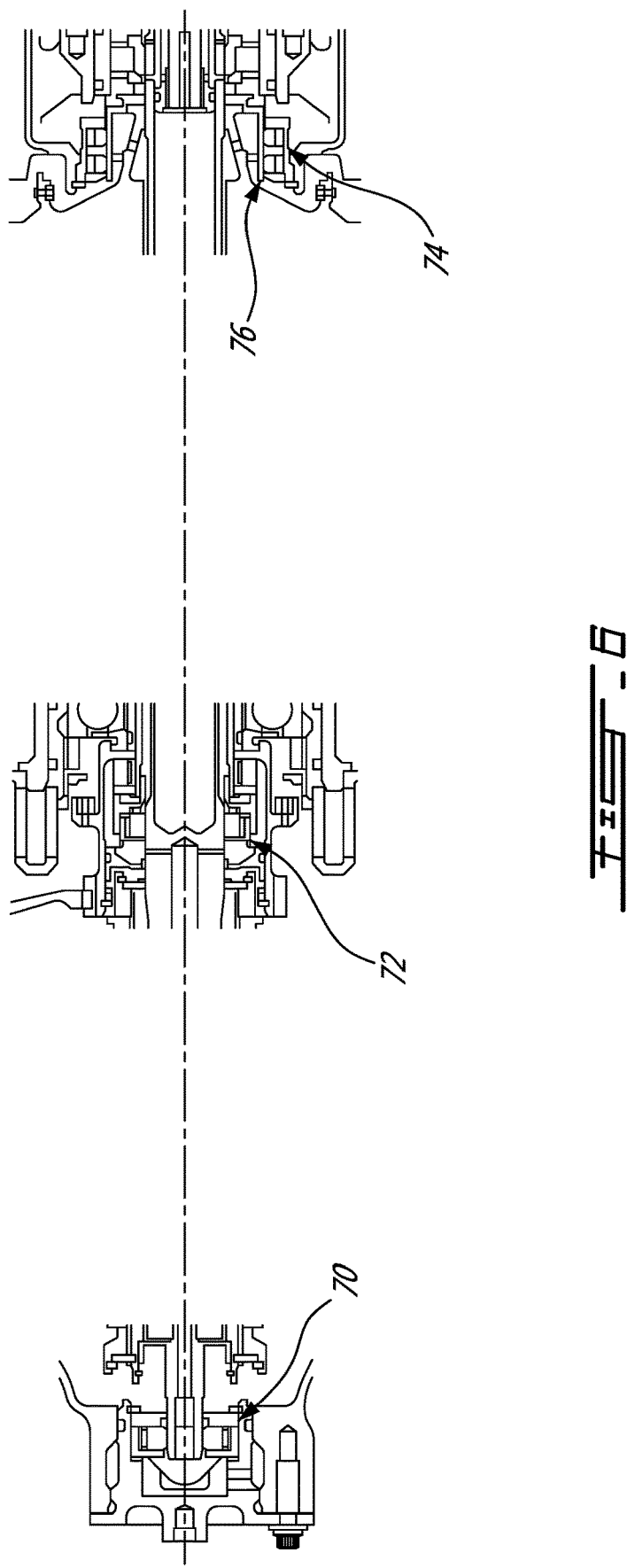

METHOD OF IDENTIFYING A SOURCE COMPONENT OF PARTICULATE DEBRIS IN AN AIRCRAFT ENGINE

TECHNICAL FIELD

The application relates generally to maintenance and diagnostic of aircraft engines and, more particularly, to a method of identifying a source component of particulate debris.

BACKGROUND OF THE ART

In aircraft engine, some components are designed to progressively wear during engine operation and eventually be replaced. The presence of particulate material of such components in engine fluids can be normal and non-alarming. However, in some cases, the presence of particulate material in an engine fluid can be a sign of premature wear of a component or of another condition which should trigger engine maintenance. By determining the nature of the debris (e.g. metal, carbon, polymer), one can obtain an indication of the nature of the engine condition, and can guide maintenance personnel in efficiently performing engine maintenance.

Even though known methods were satisfactory to a certain degree, there remained room for improvement. In particular, there remained room for improvement in further reducing the amount of maintenance time required for a given engine.

SUMMARY

In one aspect, there is provided a method of identifying a source component of particulate carbon debris collected from an aircraft engine, the method comprising: analyzing the composition of the particulate carbon debris, including ascertaining a presence of at least one main composition element and a presence or absence of at least one signature element in the particulate carbon debris; establishing a correlation between the particulate carbon debris and a set of components, including matching the ascertained presence of the at least one main composition element to a family of carbon materials from which the components of the set, including the source component, are made; and determining the source component amongst the components of the set, including matching the ascertained presence or absence of the at least one signature element to a carbon composition of the source component.

In another aspect, there is provided a gas turbine engine comprising a set of components, the components of the set all being made of carbon compositions of the same family of carbon materials having a common at least one main composition element, the carbon compositions having distinct signatures in the form of a varying trace amount of one or more signature element, the distinct signatures varying from one component of the set to another.

In a further aspect, there is provided a gas turbine engine comprising a set of components, the components of the set all being made of material compositions of the same type having a common at least one main material element, the material compositions having distinct signatures in the form of a varying trace amount of one or more signature element, the distinct signatures varying from one component of the set to another.

DESCRIPTION OF THE DRAWINGS

Reference is now made to the accompanying figures in which:

FIG. 6 is a cross-sectional view of portions of a gas turbine engine showing an example set of carbon seal components.

DETAILED DESCRIPTION

Figure 1:
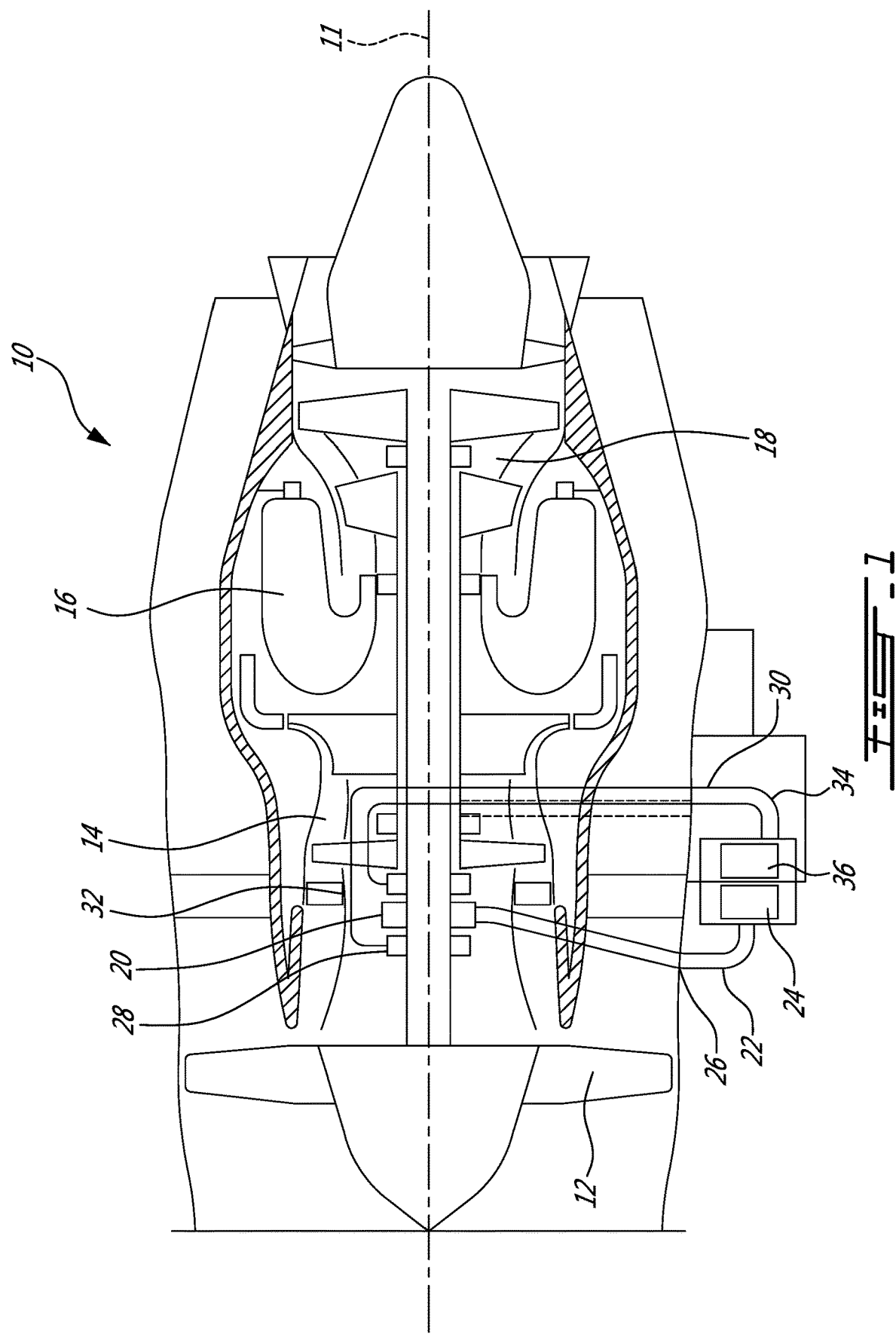
FIG. 1 is a schematic cross-sectional view of a gas turbine engine.

FIG. 1 illustrated a gas turbine engine 10 of a type preferably provided for use in subsonic flight, generally comprising in serial flow communication a fan 12 through which ambient air is propelled, a compressor section 14 for pressurizing the air, a combustor 16 in which the compressed air is mixed with fuel and ignited for generating an annular stream of hot combustion gases, and a turbine section 18 for extracting energy from the combustion gases.

The compressor 14, fan 12 and turbine 18 have rotating components which can be mounted on one or more shafts. Bearings 20 are used to provide smooth relative rotation between a shaft and casing (non-rotating component), and/or between two shafts which rotate at different speeds. An oil lubrication system 22 including an oil pump 24, sometimes referred to as a main pump, and a network of conduits and nozzles 26, is provided to feed the bearings 20 with oil. Seals 28 are used to contain the oil. A scavenge system 30 having cavities 32, conduits 34, and one or more scavenge pumps 36, is used to recover the oil, which can be in the form of an oil foam at that stage, from the bearings 20.

Figure 2:
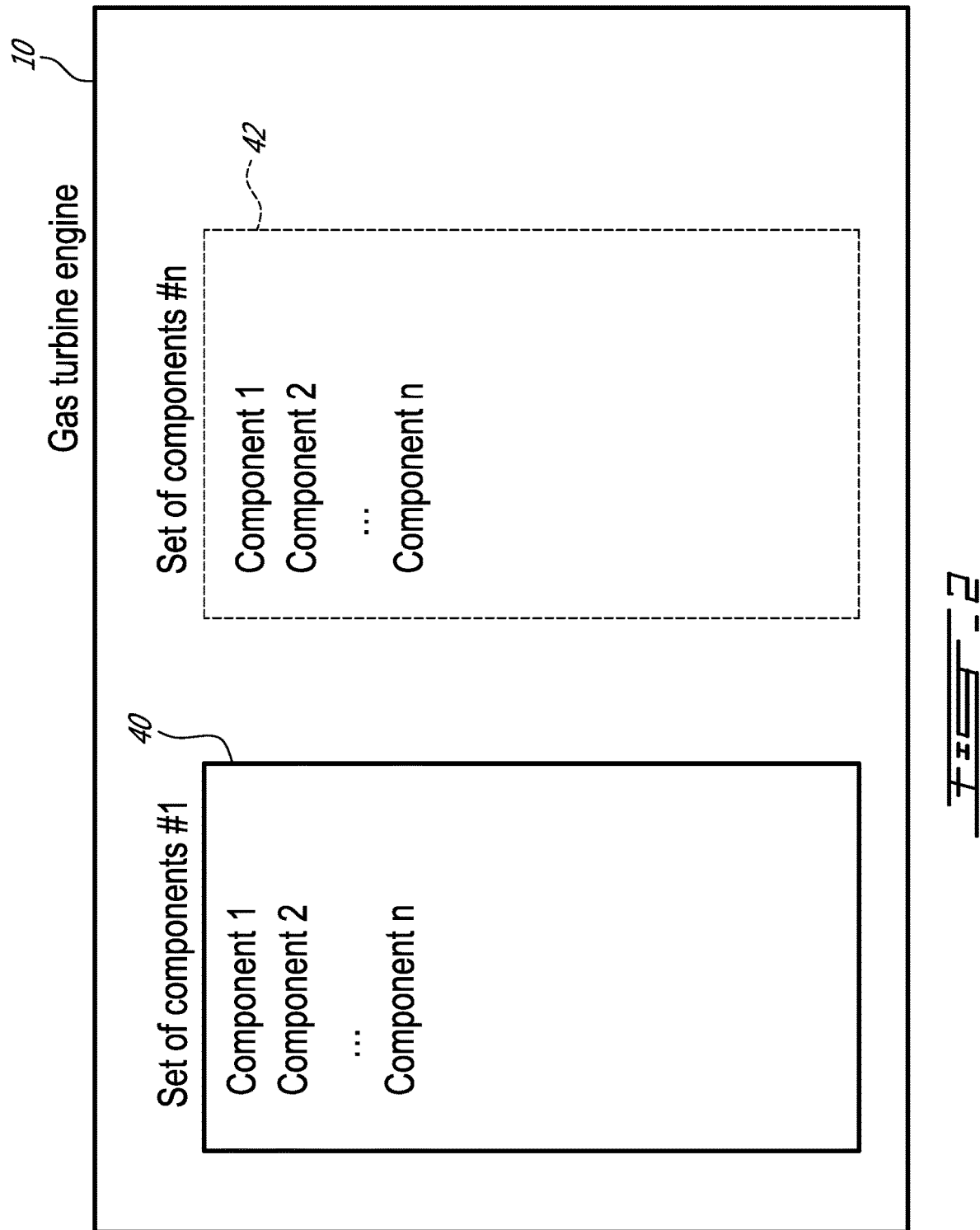
FIG. 2 is a block diagram of a gas turbine engine.

Many gas turbine engines, such as the gas turbine engine 10 of FIG. 1, schematized in FIG. 2, include one or more sets of components 40, 42. In one example, a gas turbine engine can include a plurality of bearing assemblies where each bearing assembly is positioned at a given axial position and facilitates rotation and relative positioning at a rotary interface between a given combination of component portions. Bearing assemblies can include a plurality of sets of components. For instance, each bearing assembly can include a corresponding bearing cavity in which a corresponding bearing is enclosed, the bearing cavity being terminated by corresponding seals. The plurality of seals associated with the different bearing assemblies of a given engine can be referred to as a set of seals, and the plurality of bearings can be referred to as a set of bearings. Typically, bearing cavities including seals and bearings are provided between rotary and non-rotary components, or between two components which rotate at a different speed (such as high pressure shaft and low pressure shaft), wherein the rotary components rotate around the engine's main axis 11. However, bearings and seals can also be associated to components which rotate around axes different from the main axis 11, such as auxiliary shafts or power shafts of turboshaft or turboprop engines.

Many seals are made of carbon compositions, typically a composite material including a relatively high concentration of carbon in a polymer matrix. However, other sets of components can be configured to accommodate potential rubbing between components which rotate relative to one another. For instance, some gas turbine engines can have a set of polymeric materials, such as polymeric bushings, which are secured or otherwise integrated with non-rotary components, and are configured to be occasionally rubbed against by rotating components in certain engine operation conditions. Even in the case of rotary interfaces between components, some seals are directly made of metal alloys rather than making use of composite materials.

Some gas turbine engines can also include one or more sets of rotating components such as gears, shafts, or the like. Such rotating components are typically made of metals, and in the field of aerospace/aeronautics, much consideration can be given to the exact choice of alloy to optimize the materials for corresponding functions and for corresponding contexts.

Many contact interfaces between relatively moving components, such as between rotary and non-rotary components, between components that rotate at different speeds, or components which may otherwise occasionally rub against one another, have wearable components, i.e. components which are design to wear over time due to rubbing, abrasion, or the like. Typically, wearable components are designed to wear more easily than a component which is rubbed against it, in a sacrificial manner, meaning that the wear component is designed to be changed once it has worn by a certain amount, whereas the condition of the component which has rubbed against it has been preserved throughout the wear. \Near components can include carbon seals and polymer bushings, for instance, but can also include some alloys.

Many contact interfaces are exposed to a recirculated lubrication fluid such as oil, in a manner to lubricate the components and limit wear. In the case of gas turbine engines, as new oil gradually replaces previously sprayed oil, the previously sprayed oil is eventually gathered by the bearing cavity, scavenged, and circulated across a filter and air/oil separator, and recycled as new oil. Particles of various components at the interfaces can thus be collected by the oil, and eventually captured by a filter or the like, or collected in an oil reservoir. Scavenged particle analysis can be performed on such captured/collected particles. Using basic equipment, such as a microscope for instance, it is typically relatively easy to distinguish between entirely different materials, such as between carbon, polymer, and even different alloys such as steel and Inconel. However, scavenged particle analysis can be pushed further, typically using more elaborated equipment, and even determine the composition of scavenged particles. While some wear components are expected to wear at a certain rate, scavenged particle analysis may also allow to detect the presence of particles associated with components which are not supposed to wear, or even establish an abnormal quantity of particles of a component which is expected to wear. Such detections can be indicative of premature wear of a component, or even engine malfunction, and may trigger a further investigation and associated engine maintenance.

The analysis of the detected particles may not allow to single out a given component, from a set of components, which causes the issue. For instance, the particle analysis may allow to establish that there is a premature wear of a carbon seal, while not allowing to single out which carbon seal, amongst the set of carbon seals of a given engine, is being subjected to premature wear. The same can be said about different interface portions of shaft(s) from a set of engine components made of a similar alloy, or different polymer bushings from a set of polymer bushings, for instance. The maintenance personnel therefore has a relatively large field of investigation, and may require a significant amount of maintenance time, and disassembly of a large amount of components, before being able to conclusively establish the source of the premature wear. Since maintenance time has a direct relationship with maintenance costs, there was a need to reduce the amount of maintenance time, and accordingly, there can be a need to allow maintenance personnel to obtain more information about the identity of the component which is the source of the identified problem or concern, in a manner to narrow the field of investigation of maintenance personnel, and ultimately reduce maintenance time.

For instance, if a carbon seal starts to spin and rub against its static housing, maintenance personnel may appreciate receiving an indication that the debris stems from carbon rubbing against its housing as opposed to carbon rubbing against a turning shaft. Further receiving an indication of which carbon seal is so behaving may even further assist maintenance personnel in focussing their maintenance time on the correct seal, instead of disassembling a larger number of components to access a larger number of seals for visual inspection.

Henceforth, in accordance with one aspect, there is provided a gas turbine engine having a set of components associated with corresponding interfaces between rotary and non-rotary components and/or between components rotating at different speeds, wherein the individual components of the set are made of the same type, or family, of material (e.g. carbon composite, polymer, given alloy type), but where the exact material composition of each component of the set differs discernably, even though slightly, from the material of the other components of the set. More specifically, each component of the set can be made of a material composition having a unique signature amongst the components of the set. The distinct signature can be in the form of a varying trace amount of one or more elements which may be present in such low quantities so as to have no significant effect on the material properties of the set, while still being present in a sufficient concentration so as to allow distinguishing its presence from an impurity.

The difference can be in the form of the presence of different trace elements, different concentrations of a given trace element, different combinations and/or concentrations of trace elements, to name some examples. The concentration of the trace element(s) can be selected in a manner to be sufficient to allow to detect it, or to allow to differentiate the relative concentrations of the trace element in different components of the set, while not being sufficient to significantly affect the functionality of the component. The trace element can thus be used specifically for the purpose of traceability as to the source component from a set of components of eventual particles which are collected, such as particles collected by the scavenge system for instance.

Accordingly, once the particles have been collected, they can be analyzed so as to characterize their composition, yielding a list of distinct elements forming the composition, and possibly even a concentration of such elements in the composition of the particulate debris. Some of the elements can be main elements of a given material family, or otherwise said, the basic ingredients forming the corresponding type of material composition. For instance, stainless steel is known to include an important concentration of Fe, whereas carbon composites of carbon seals are known to include important concentrations of carbon. One or more other elements, referred to herein as signature elements, can be introduced, or their concentrations modulated, in a manner to form slight but measurable distinctions between the different components of the set. For instance, varying concentrations of tin or lead can be added to different ones of the carbon seals, or varying concentrations of gold, silver and/or platinum can be added to different ones of the carbon seal housings, or to different ones of the gears, for instance. The expression "element" is used herein for the sake of simplicity, and it will be understood that the main elements and the signature elements can be in the form of molecules instead of atoms in some cases.

Figure 3:
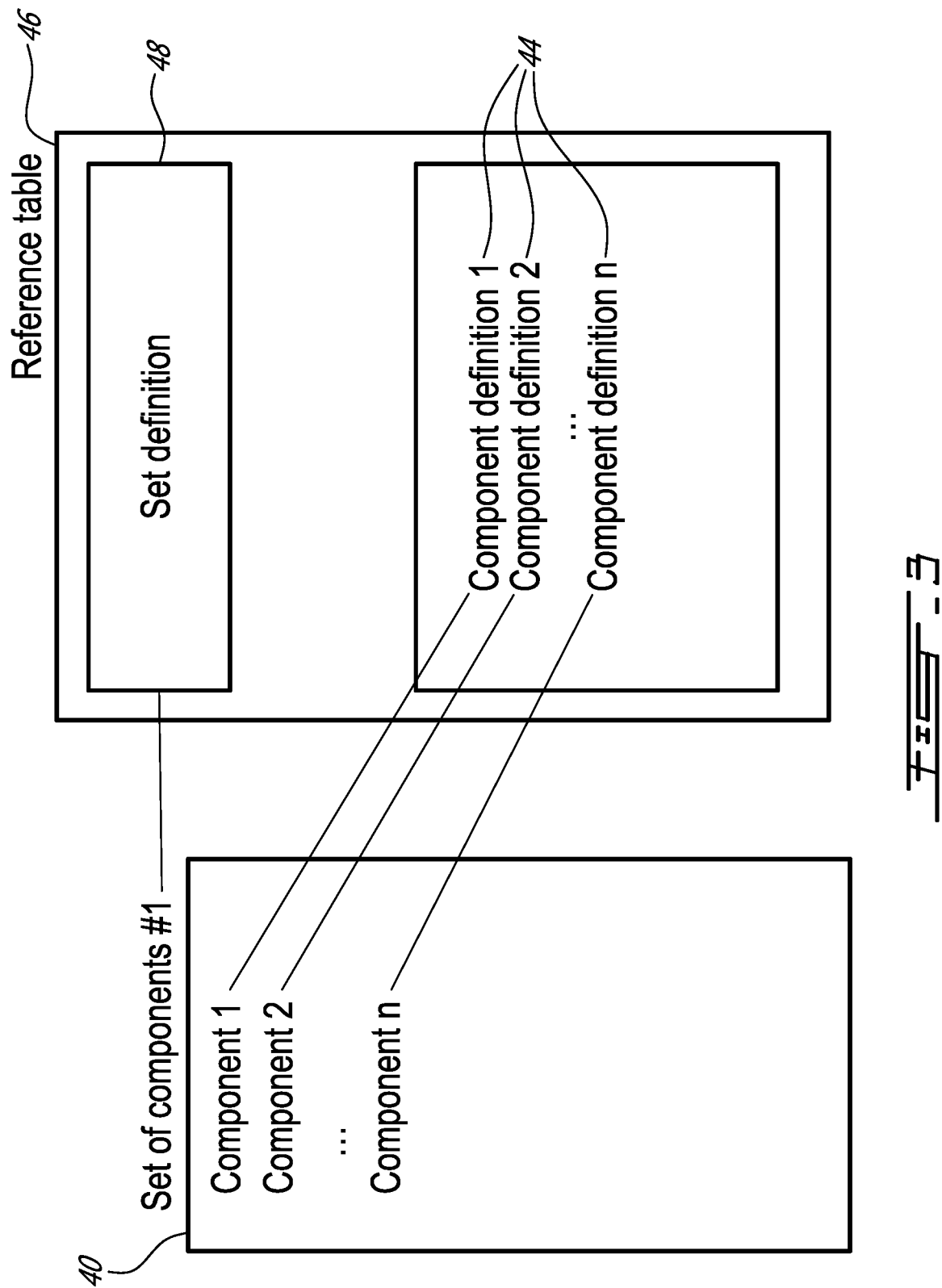
FIG. 3 is a block diagram of a reference table, illustrating the relationship with the gas turbine engine of FIG. 2.

Referring to FIG. 3, each component of the set can become encoded with a specific presence, absence, or proportion of one or more signature element. This coding can be preserved once the components of the sets are assembled into the aircraft engine. For instance, the carbon seals of the #1 bearing can be components 1 and 2, the carbon seals of the #2 bearing can be components 3 and 4, and so forth, and each of the components 1 to n can have a specific "component definition" 44 allowing to determine its signature upon analysis of particulate debris therefrom. The definition for a given component may be the detailed composition, or may be simplified in a manner to contain only a combination of elements, and may additionally specify threshold concentrations for such elements. The definitions can be stored in the form of a reference table 46 which can be printed on paper, or stored as data in a computer readable memory, to name two examples.

In some cases, such as in an embodiment where one is only interested in carbon seals for instance, it may be easy to differentiate particulate debris stemming from carbon seals from particulate debris stemming from other engine components, and therefore ascertaining the set of components may be straightforward, and the challenge will only lie in determining which one of the components of the set is the source of the debris. In other cases, one may be interested in tracking debris from more than one set of components on a given engine, and a preliminary step of determining which set of components the particular particulate debris comes from may be required before being able to identify which one of the components of that set is the source of the particulate debris. To this ends, different sets can be attributed different "set definitions" 48 allowing to distinguish, in a given aircraft engine, which "set of components" the debris is attributable to. The set definitions can be more or less elaborated depending on the application. Generally, the set definitions will typically include the identification of one or more main element of the type of material composition family (e.g. Fe, C, a polymer string, etc). In some embodiments, the set definitions can additionally specify threshold concentrations for one or more main element detected. Similarly to the component definitions, the set definitions can be stored in the form of a reference table which can be printed on paper, or stored as data in a computer readable memory, to name two examples.

The definitions may not be exhaustive in some embodiments, and simply define a minimum threshold concentration value (e.g. to ascertain a presence), a maximum threshold concentration value, both a minimum and a maximum threshold values defining a range. In some embodiments, by having a signature element on top of a general proportion, the detection system can release certainty threshold about a particular alloy. So before the detected proportions of a certain stainless steel elements match the detection criteria (ex.: 2-3% Ni, 6-15% Cr, >50% Fe), as long as the signature element is detected along with the other ones, the presence of that specific alloy can be confirmed. In that case, there is no need to match proportion before being sure about the presence of an alloy. Typically, the definition will include at least a nature of an element, and optionally a concentration range or threshold for that element.

In alternate embodiments, the component definitions may be sufficiently exhaustive by themselves to allow to perform a complete segregation of the components from one another without having to perform a prior segregation between sets of components, for example.

Figure 4:
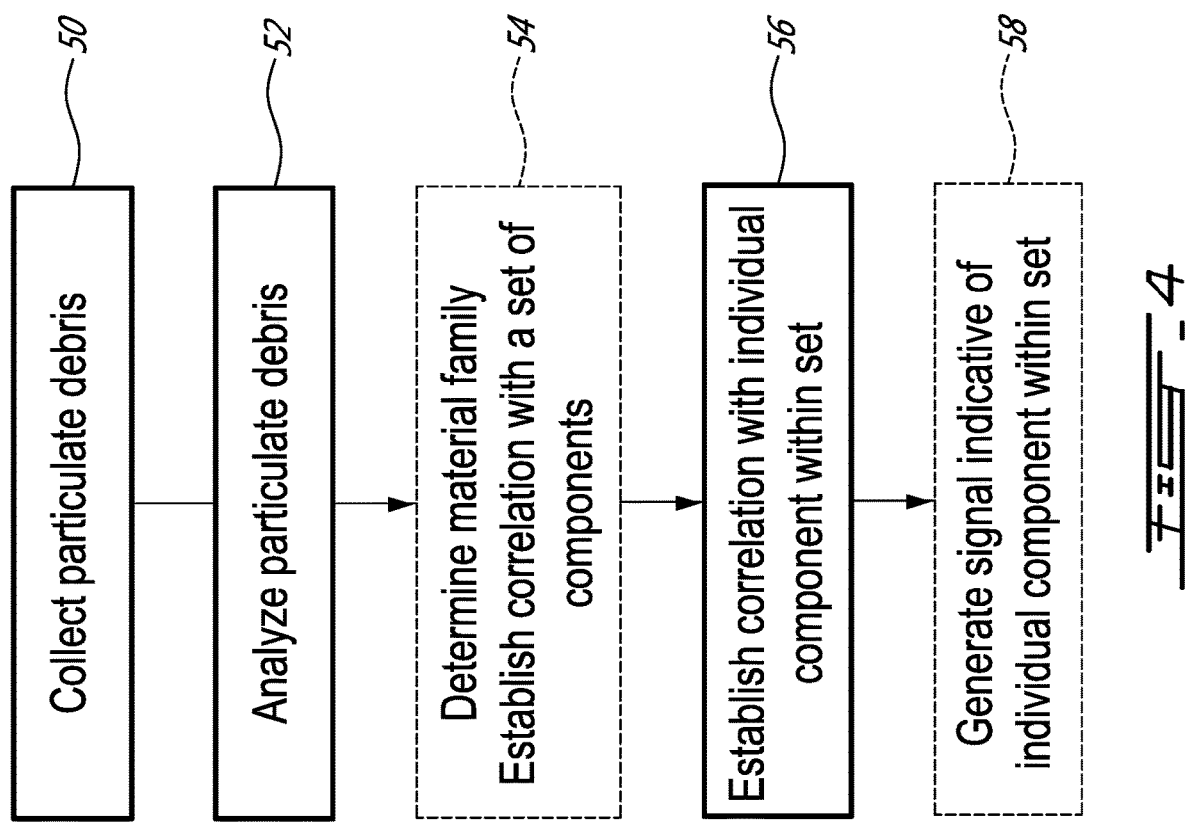
FIG. 4 is a flow chart of a method of determining a source component from particulate debris.

Accordingly, with reference to FIG. 4, once particulate debris collected 50 from an aircraft engine has been analyzed 52, the presence of at least one main element, and a presence or absence of at least one signature alloy element have been ascertained, a correlation can be established between the particulate debris and a specific set of components 54, and further between the particulate debris and a specific one of the components of the set 56. For instance, the correlation between the particulate debris and the set of components can be established on the basis of matching the detected presence of the one or more main alloy element with a corresponding set definition. The correlation with the specific component of the set as being the source component can be established on the basis of matching the detected presence or absence of the signature element with a corresponding component definition. In some embodiments, the correlations and matches can be established by a computer which is provided access to the data concerning the elements which were detected in the particulate debris, and the definitions, and the computer generates a signal indicative of an individual component within the set 58, whereas in other embodiments, the correlation and matching can be made by maintenance personnel.

In some embodiments, rather than just ascertaining a presence or absence of a given element, it can be considered useful to measure the concentration of the given element, and to compare it to a corresponding threshold included in the corresponding definition, in a manner to allow making the determination.

The collection of the particulate debris can be performed in various ways and the exact choice can depend on the specificities of the given application. For instance, particulate debris can be present in the form of dust on a solid surface and can be collected directly from the surface, it can be present in a fluid of the engine, such as the oil for instance, and the oil itself can be collected and analyzed. Moreover, some engines use magnetic chip collectors in the oil flow, and the magnetic field of such chip collectors can maintain chips attracted even when the engine has stopped. And to name another example, particulate debris can be collected directly from an oil filter.

Some examples will now be presented for additional clarity.

Alloy Example

A fleet can be managed by trend monitoring engine condition. For instance, trend monitoring can be performed to plan maintenance activities and/or prevent failures by detecting early signs of wear/failures. Such monitoring can be done by analyzing the nature of oil particle content or filter debris.

In order to be able to trace the source of failures and/or monitor engine/component condition, the alloying content of a recurring main alloy can be varied from one component to another in a manner for its presence to be detectable.

This can be done by adding specific element to the alloy formula (as shown in example below) to a level that doesn't interfere with its physical or mechanical properties while still being detectable.

Example of Alloys Modulation:

AMS6000 contains: Fe 10%, Ni 20%, Cr 70%

AMS6000B contains: Fe 10%, Ni 20%, Cr 70%, signature element #1 0.1-0.2%

AMS6000C contains: Fe 10%, Ni 20%, Cr 70%, signature element #2 0.3-0.4%

Wear rate or failure events can become traceable and components can be segregated from one another.

This can be coupled with trend a monitoring system (e.g. oil analysis, chip analysis, debris filter analysis or other) and data analysis.

To the extreme, every single part of the engine could be made out of slightly different alloys (x modulations of main alloys). When an event occurs, precise knowledge of affected components and even sequence of event could be understood based on dust collection analysis or oil content analysis.

Every component can be made of an alloy having a single signature.

In some more limited examples, alloy modulation can be applied to sets of gears (AGB gears, RGB gears), sets of bearings (RGB, main shafts), sets of seals (main shaft seals, AGB seals) or sets of other parts for which progressive failure might occur.

Figure 5:
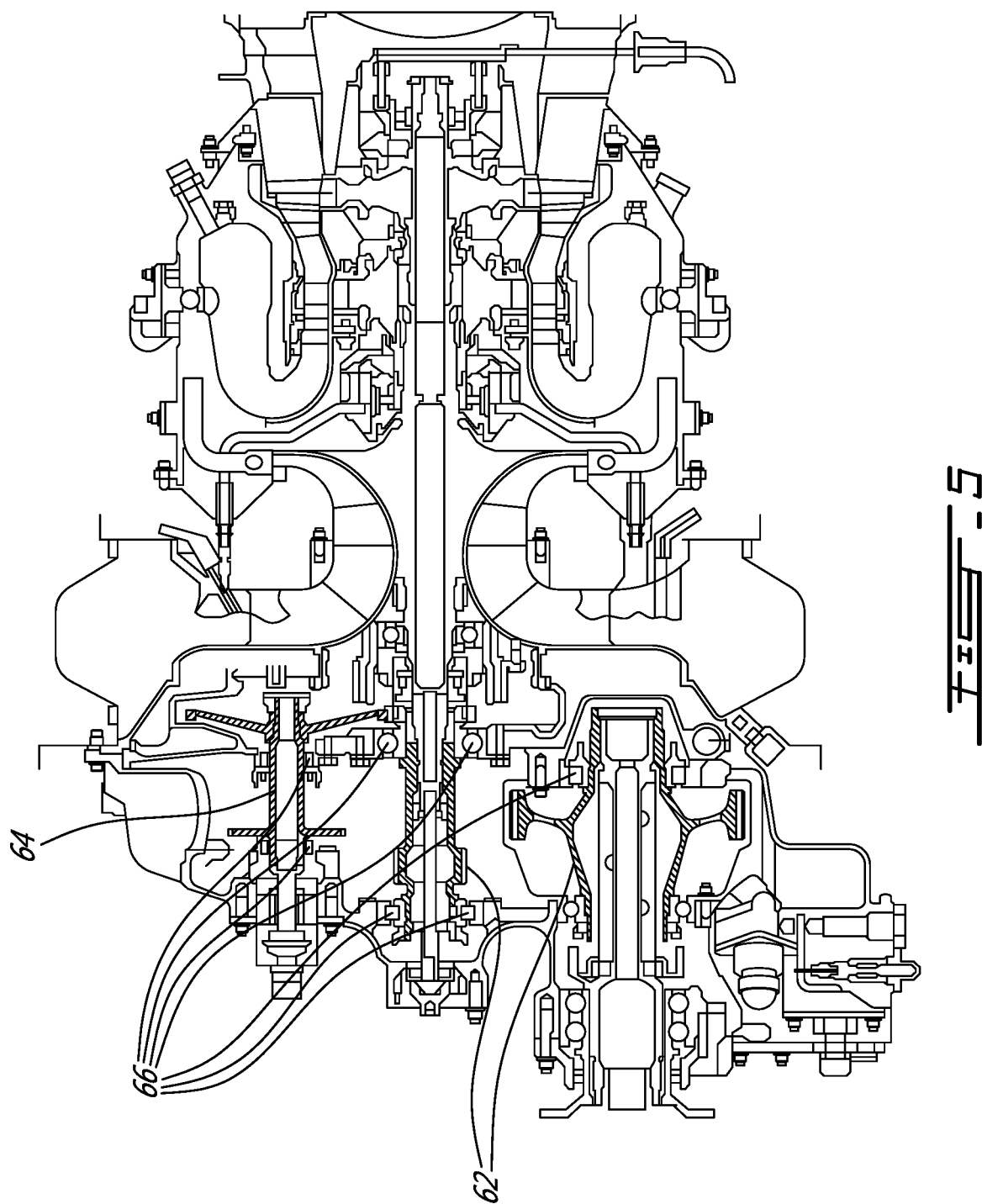
FIG. 5 is a cross-sectional view of a gas turbine engine showing example sets of alloy components.

FIG. 5 shows an example where sets of gears 62, 64, and sets of bearings 66 which can be made out of alloy modulations.

For instance, every gear of the same gear train can be made of similar steel with slight signature element modulation, allowing detecting which one is failing/wearing. For smaller sets, this can represent less than 10 variations of the same alloy.

The gold lots can be identified in this manner (alloying elements added in low quantities) to trace their origins. The segregation of alloy can be done for trend monitoring purpose and/or failure event understanding.

Instead of adding different elements, different proportions of the same added element can be added to the alloy to get low but detectable physical/mechanical properties variations.

Carbon Example

Carbon seals on turbine engine generally wears and their condition affects engine performance.

Carbon is generally used for its favorable friction behavior to seal rotating interfaces. The carbon elements are generally placed between a rotating surface and a static structure holding it in place. The face that touches or at risk of touching the rotating surface is subject to wear. There is a need and a general desire to closely monitor wear and/or wear rate and/or seal condition through the life of the engine in order to ease maintenance and/or prevent failures. Detection methods and big data/trend monitoring systems can be used as fleet management methods. FIG. 6 shows three carbon seals which can have components 70, 72, 74, 76 made of different carbon compositions. Sealing surface configurations can be radial or axial.

In order to be able to trace the source of failures and/or monitor individual seal condition, the material content of a recurring main carbon grade can be varied in a detectable manner.

This can be done by adding a specific element to carbon composition formula (as shown in example below). The amount of added element may be insufficient to significantly affect the performance of the seal (physical or mechanical properties) while being sufficient to be detectable. The signature element can have uniqueness to more clearly distinguish from standardized materials already used in the production process.

Example of Carbon Composite Modulation:

Carbon #1 contains C 80%, O 18%, Ca 1%

Carbon #1B contains: C 80%, O 18%, Ca 1%, other element #1 0.1-0.3%

Carbon #1C contains: C 80%, O 18%, Ca 1%, other element #2 0.4-0.5%

Wear rate or failure events can thus be traceable and components can be segregated from one another. This can be coupled with trend monitoring systems (oil analysis or others) and data analysis activities.

This can be done in phase with debris monitoring systems being deployed on latest engine programs. This would allow to prevent failures or plan maintenance activities.

As prior art, the gold lots can be identified in this manner (alloying elements added in low quantities) to trace their origins. In the case of this disclosure, the segregation of alloy would be done for trend monitoring purpose and/or failure event understanding.

Every seal is made of a carbon having a single signature. Instead of various elements, it could be various proportions of the same added element or working on the composition to get low but detectable physical/mechanical properties variations (radioactivity, electrical, magnetism).

The same concept could be applied to another material with favorable frictional properties.

Alternate Embodiments

It will be understood that in some embodiments, the set of components can include a plurality of components having the same function in the gas turbine engine, but located at different positions in the gas turbine engine. More specifically, the different components of the set can be located at corresponding contact interfaces, such as rotary interfaces where the component can come into contact with another component of the aircraft engine. The components of the set can be components which have different functions, but which are made of the same type of alloy for instance. The components of a given set can be one or more of a shaft, a bearing, a gear, and a shaft mounted feature. In other embodiments, all the components can be of the same functionality, such as all being part of a shaft, all being gears, all being bearings, for instance.

In the case of sets of components all made of a given alloy family, the alloy family can be steel, stainless steel, nickel, titanium, aluminum, to name some examples, and in which case the signature element can be one or more of gold, silver, tungsten and platinum to name some possible examples.

In the case of sets of components all made from a given family of carbon materials, the carbon material can be a composite including carbon particles in a polymer matrix for instance, and the signature element can be one or more of tin and led for instance.

In the case of sets of components all made from a given family of mechanical polymers, the mechanical polymer can be PEEK, Polyketone, Polyamid or Polyimid for instance, and the signature element can be one or more of tin and led for instance, or any other suitable detectable material The proportion of the signature element can vary in different embodiments. It can be preferred in some embodiments to keep the concentration low to avoid a scenario where adding the tracing ability would interfere with the material's mechanical or physical properties. For instance, in some cases, it can be preferred to keep the concentration of the signature element below 3% by weight, preferably below 1% by weight, and more preferably below 0.5% by weight. On the other hand, it is known in the production of alloys, mechanical polymers and carbon materials that some level of impurities can be considered normal and acceptable, and it may be preferred to maintain the concentration of the signature element above such an impurity threshold to allow to differentiate the signature element from an impurity. To this end, it can be preferred to maintain the concentration of the signature element above 0.01% or above 0.02% for instance.

The embodiments described in this document provide non-limiting examples of possible implementations of the present technology. Upon review of the present disclosure, a person of ordinary skill in the art will recognize that changes may be made to the embodiments described herein without departing from the scope of the present technology. Yet further modifications could be implemented by a person of ordinary skill in the art in view of the present disclosure, which modifications would be within the scope of the present technology.

The invention claimed is:

1. A method of identifying a source component of particulate carbon debris collected from an aircraft engine, the method comprising:
   analyzing the composition of the particulate carbon debris, including ascertaining a presence of at least one main composition element and a presence or absence of at least one signature element in the particulate carbon debris;
   establishing a correlation between the particulate carbon debris and a set of components, including matching the ascertained presence of the at least one main composition element to a family of carbon materials from which the components of the set, including the source component, are made; and
   determining the source component amongst the components of the set, including matching the ascertained presence or absence of the at least one signature element to a carbon composition of the source component.

2. The method of claim 1 wherein the steps of establishing and determining are performed by a computer, further comprising the computer generating a signal indicating the identity of the source component.

3. The method of claim 1 wherein the analyzing includes performing oil analysis of oil from the aircraft engine.

4. The method of claim 1 wherein the analysing the composition includes measuring a concentration of the at least one main composition element in the particulate carbon debris, and wherein the step of matching the ascertained presence of the at least one main composition element includes comparing the measured concentration to at least one threshold value associated with a definition of the family of carbon materials.

5. The method of claim 4 wherein the concentration of the at least one main composition element is of above 1%.

6. The method of claim 1 wherein the analyzing the composition includes measuring a concentration of the at least one signature element in the particulate carbon debris, and wherein the step of matching the ascertained presence or absence of the at least one signature element includes comparing the measured concentration to at least one threshold value associated with a definition of the of the source component carbon composition.

7. The method of claim 6 wherein the concentration of the at least one signature element is of between 0.01 and 0.1%.

8. The method of claim 1 wherein the set of components includes a plurality of components having the same function in a gas turbine engine, but located at different positions in the gas turbine engine.

9. The method of claim 8 wherein the set of components is a set of carbon seals.

10. The method of claim 1 wherein the family of carbon materials have a common at least two main composition elements including carbon in a polymer matrix.

11. The method of claim 10 wherein one of said signature element is tin or lead.

12. The method of claim 1 further comprising collecting the particulate carbon debris from the aircraft engine.

13. The method of claim 12 wherein the particulate carbon debris is collected by collecting dust from the aircraft engine.

14. The method of claim 12 wherein the particulate carbon debris is collected by a chip collector of the aircraft engine.

15. The method of claim 12 wherein the particulate carbon debris is collected from a filter of the aircraft engine.

* * * * *